United States Patent [19]

Hachmuth et al.

[11] Patent Number: 4,677,244

[45] Date of Patent: Jun. 30, 1987

[54] CATALYTIC ALKYLATION PROCESS AND APPARATUS

[75] Inventors: Henry K. Hachmuth; Keith W. Hovis, both of Bartlesville, Okla.

[73] Assignee: Phillips Petroleum Company, Bartlesville, Okla.

[21] Appl. No.: 804,730

[22] Filed: Nov. 29, 1985

[51] Int. Cl.$^4$ .................. G05D 23/00; G05D 23/12
[52] U.S. Cl. .................. 585/701; 422/109; 422/111; 422/112; 436/55; 436/147; 436/148; 585/710
[58] Field of Search .................. 436/55, 147, 148; 422/109, 112, 62, 106, 111; 585/701, 707, 709, 710

[56] References Cited

U.S. PATENT DOCUMENTS

| | | | |
|---|---|---|---|
| 3,200,883 | 8/1965 | Phillips | 585/701 |
| 3,206,524 | 9/1965 | Plaster | 260/683.42 |
| 3,211,802 | 10/1965 | Dixon et al. | 260/683.45 |
| 3,213,157 | 10/1965 | Hays et al. | 260/683.48 |
| 3,431,079 | 3/1969 | Chapman | 23/260 |
| 3,763,266 | 10/1973 | Henderson | 260/683.48 |
| 3,819,917 | 6/1974 | Sweeney, Jr. et al. | 585/707 |
| 3,825,616 | 7/1974 | Chapman | 260/683.48 |
| 3,897,487 | 5/1975 | Vora | 260/683.48 |
| 4,059,649 | 11/1977 | Chapman et al. | 260/683.48 |
| 4,123,351 | 10/1978 | Chapman et al. | 208/262 |
| 4,189,616 | 2/1980 | Liebert | 585/701 |
| 4,205,196 | 5/1980 | Makovec et al. | 436/55 |
| 4,224,283 | 9/1980 | Potts | 422/111 |
| 4,236,036 | 11/1980 | Dixon et al. | 585/331 |
| 4,290,110 | 9/1981 | Makovec | 436/55 |
| 4,476,094 | 10/1984 | Carson | 422/112 |
| 4,482,969 | 11/1984 | Funck et al. | 422/62 |

Primary Examiner—Michael S. Marcus
Attorney, Agent, or Firm—George E. Bogatie

[57] ABSTRACT

An apparatus and method for manipulating the temperature and pressure of the hydrocarbon phase in an acid settler vessel associated with a catalytic alkylation process and apparatus, wherein the hydrocarbon phase in the acid settler vessel is regulated by controlling the amount of rerun catalyst stream entering the hydrocarbon phase of the acid settler vessel. In response to a detected temperature or pressure of the hydrocarbon phase above a set point, the flow of rerun catalyst stream to the hydrocarbon phase of the acid settler vessel is decreased. This decrease in flow to the hydrocarbon phase may be accompanied by an increase in flow of rerun catalyst vapor to the catalyst phase of the acid settler vessel.

8 Claims, 1 Drawing Figure

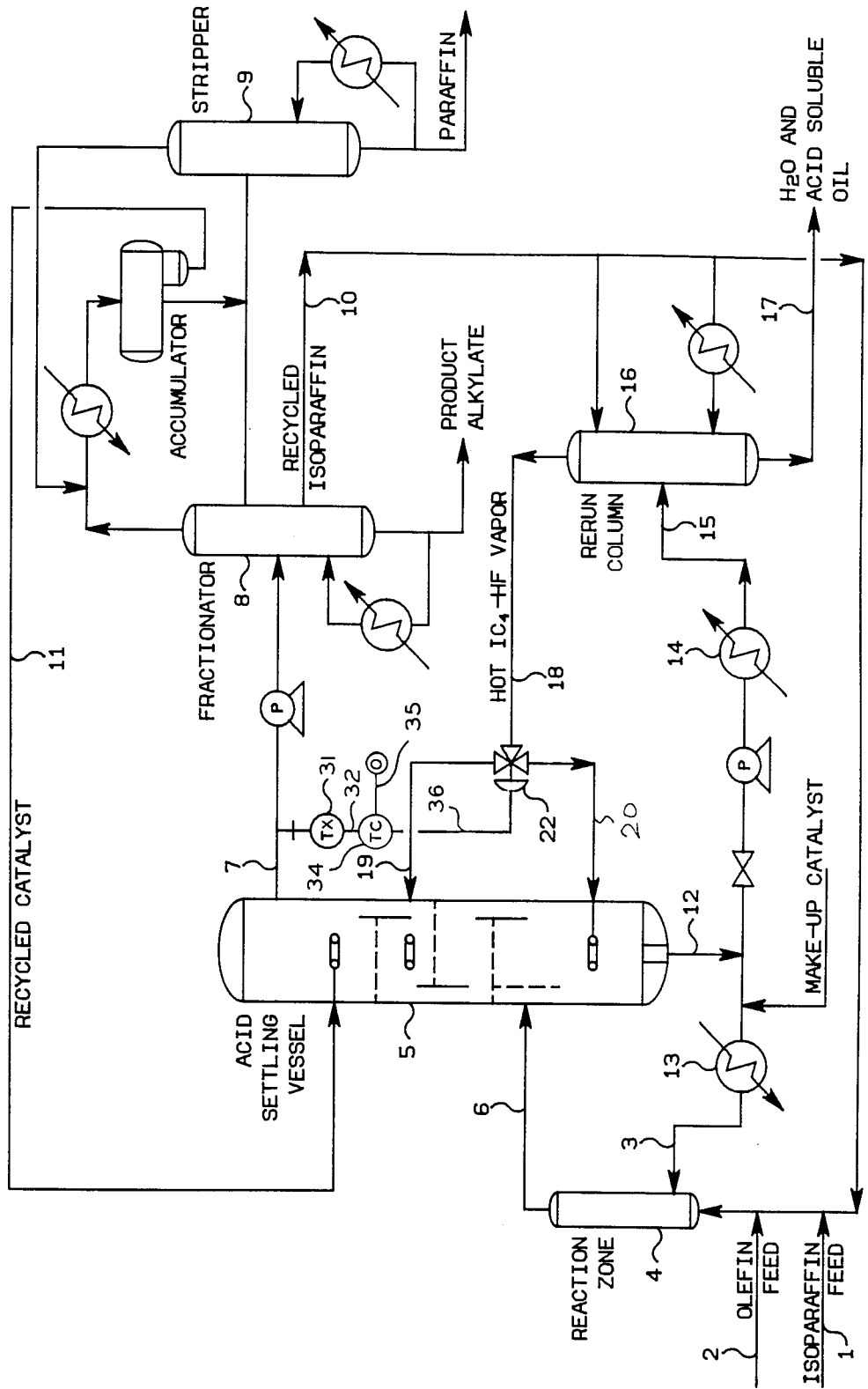

CATALYTIC ALKYLATION PROCESS AND APPARATUS

BACKGROUND OF THE INVENTION

The invention relates to a catalytic alkylation process and apparatus. In one embodiment, the invention relates to the control of temperature in the hydrocarbon phase of an acid settler vessel in a catalytic alkylation process and apparatus.

Numerous processes are known in the prior art for alkylating an alkylatable hydrocarbon such as an isoparaffin with an alkylating agent such as an olefin in the presence of a catalyst. A successful commercial system involves the circulation of an acid-type catalyst, such as hydrofluoric acid or sulfuric acid, through a reaction zone, a separation zone, a cooling zone and back to the reaction zone.

In one such process for the alkylation of hydrocarbons, hydrocarbons are introduced into the acid catalyst in the lower portion of an alkylation reaction zone maintained at suitable alkylation reaction conditions. A stream comprising catalyst, alkylate product and unconsumed reactants rises through the reaction zone and passes from the upper portion of the reaction zone into a catalyst settling zone, wherein separation occurs between the hydrocarbon phase and the catalyst phase. Catalyst withdrawn from the catalyst phase of the settling zone is cooled and returned to the reaction zone. Such a process involves cyclic catalyst flow through the system. A hydrocarbon stream is withdrawn from the hydrocarbon phase for further processing, including fractionation of unreacted isoparaffin from the alkylate product.

It is known that the presence of excessive amounts of water in the acid catalyst is highly corrosive to the alkylation and catalyst handling systems. Although the acid catalyst is normally utilized in an essentially anhydrous condition, there is a tendency in alkylation systems for water to accumulate as the acid catalyst is repeatedly recycled through the system. It is also known that a material known as acid-soluble oil is produced in the alkylation reaction, and that this material acts as a diluent for the catalyst phase. In general, the production of acid-soluble oil is substantially in excess of that necessary or desirable for dilution of the catalyst.

Consequently, it is common for alkylation systems employing acid-type catalysts to include a so-called catalyst "rerun" system through which at least a portion of the catalyst is passed to remove water and acid-soluble oil. The rerun process can involve withdrawing a portion of the catalyst phase as it flows from the acid settler vessel back to the reactor. The withdrawn catalyst phase is heated to a temperature sufficient to cause separation into a liquid phase, comprising predominately water and some acid-soluble oils, and a vapor phase comprising predominately catalyst, unreacted feed materials and some alkylate. The heated catalyst phase is passed into a catalyst rerun separator column. Water and acid-soluble oil are withdrawn from the bottom of the rerun separator column while the vapor phase is recycled to the acid settler vessel.

Butadiene or other impurities present in the feed can result in higher rates of formation of acid-soluble oils in the alkylation reaction. The higher concentrations of acid-soluble oils in the alkylation reaction effluent require correspondingly higher throughputs in the rerun tower, which in turn results in more hot catalyst phase for return to the acid settler vessel. It is desirable that at least part of the hot catalyst phase be passed into the hydrocarbon phase of the acid settler vessel in order to utilize some heat from the hot catalyst phase (to maintain pressure). However, the heat of vaporization from condensation of the hot catalyst phase in the hydrocarbon phase can cause the hydrocarbon phase to undergo an excessive increase in temperature and pressure. Since the alkylation reactor is in a continuous loop with respect to catalyst flow, the introduction of high pressure acid into the reactor requires operation of the alkylate/isobutane fractionator at pressures high enough to allow the recycle isobutane to flow into the reactor. This is costly in terms of higher pressure equipment and higher pressure steam for reboiler duty. It would be possible to control the temperature of the hot catalyst phase by passing it through an external cooler, but such a cooler designed for hot acid cooling would be expensive to purchase and maintain.

It would therefore be highly desirable to provide a means for controlling the temperature of the hydrocarbon phase in the acid settler vessel without the use of expensive cooling equipment for the hot rerun catalyst. It would also be desirable to control the pressure of the hydrocarbon stream entering the alkylate/isobutane fractionator.

It is therefore an object of the invention to provide a catalytic alkylation process and apparatus. In one embodiment, it is an object of the invention to inexpensively prevent temperature and pressure buildups in the acid settler vessel of a catalytic alkylation system.

These and other objects and advantages of the invention will be apparent from the following detailed description of the invention.

SUMMARY OF THE INVENTION

In accordance with the invention, an alkylation process is provided in which the temperature (and pressure corresponding thereto) of the liquid hydrocarbon phase in the acid settler vessel is regulated by control of the amount of acid vapor from the catalyst rerun column entering the hydrocarbon phase in the acid settler vessel. In response to a detected temperature (or pressure corresponding thereto) of the hydrocarbon phase above a set point, the flow of rerun catalyst vapor to the hydrocarbon phase of the acid settler vessel is decreased. This decrease in flow to the hydrocarbon phase can be accompanied by an increase in flow of rerun catalyst vapor to the catalyst phase of the acid settler vessel.

In a specific embodiment, a catalytic alkylation reaction effluent comprising product alkylate, unreacted feed hydrocarbons and acid-type catalyst is passed into a first separation zone, wherein the reaction effluent is maintained under conditions effective to separate the reaction effluent into a hydrocarbon phase, located in the upper portion of the first separation zone, and a catalyst phase containing acid-type catalyst and acid-soluble oil, located in the lower portion of the first separation zone. A hydrocarbon stream is withdrawn from the hydrocarbon phase and the catalyst phase is separated to obtain a rerun catalyst stream comprising predominantly acid-type catalyst and alkylating agent. A first portion of the rerun catalyst stream is passed into the hydrocarbon phase located in the upper portion of the first separation zone, and a second portion of the rerun catalyst stream is passed into the catalyst phase located in the lower portion of the first separation zone.

The flow rate of the first portion of the rerun catalyst stream is varied responsive to the detected temperature or pressure of the hydrocarbon phase in the first separation zone. The flow rate of the second portion of the rerun catalyst stream can be correspondingly varied to accomodate, during times of detected high temperatures or pressure, any excess rerun catalyst which would otherwise flow to the hydrocarbon phase.

Apparatus to carry out the above process is also provided.

BRIEF DESCRIPTION OF THE DRAWINGS

The drawing is a simplified flow diagram of an alkylation system in accordance with one embodiment of the present invention.

DETAILED DESCRIPTION OF THE INVENTION

The present invention can be carried out in any type of reactor system utilizing a cyclically flowing, acid-type catalyst. The preferred system in accordance with the present invention is a cyclic catalyst system in which the mixture of hydrocarbon feed materials is maintained in a liquid state. Such a system using hydrofluoric acid HF catalyst is described in detail in U.S. Pat. No. 3,213,157.

The acid settler vessel is comprised of an upper portion, an intermediate portion and a lower portion, a design which allows for separation of the reaction effluent from the alkylation reaction zone into an upper hydrocarbon phase and a lower catalyst phase containing acid-type catalyst and acid-soluble oil. The acid settler vessel will generally contain means to separate the reaction zone effluent and the rerun catalyst into a hydrocarbon phase and catalyst phase in the acid settler vessel, such as vertical baffles positioned at the point of introduction of the reaction zone effluent to the acid settler vessel, and downcomers, contacting points and separation trays positioned in the acid settler vessel.

The acid settler vessel contains interior vertical baffles positioned adjacent to the point of introduction of the reaction effluent into the vessel and extending downwardly in the acid settler vessel. The acid settler vessel further contains contacting points positioned within the vessel at different heights and a plurality of downcomers. Each of the downcomers is associated with a contacting point. Further, the lowermost downcomer is remotely positioned from the baffle with the lower outlet of the lowermost downcomer being below the lower edge of the baffle.

A first portion of a rerun catalyst stream is passed into the upper portion of the acid settler vessel at a point below the uppermost of the plurality of contacting points. A second portion of the rerun catalyst stream is passed into a lower portion of the rerun catalyst stream at a point below the lowermost of the plurality of contacting points. The plurality of contacting points contain about three or more liquid-liquid contacting trays positioned as uppermost, intermediate and lowermost trays. The first portion of the rerun catalyst stream is passed into the acid settler vessel between the liquid-liquid contacting trays. The second portion of the rerun catalyst stream is passed into the acid settler vessel below the liquid-liquid contacting trays.

The flow of the first and second portions of the rerun catalyst stream can be varied with respect to the flow rate of the other, responsive to the measurement of a process variable (temperature or pressure) associated with the hydrocarbon phase of the acid settler vessel. The invention will be described hereinafter in terms of the measurement of temperature but a pressure measurement may be used if desired.

Conventionally the hot rerun catalyst vapor from the HF catalyst rerun column is fed to the liquid hydrocarbon phase in the acid settler vessel. This vapor stream condenses in the liquid hydrocarbon yielding heat from the condensation of the vapor which heats the liquid hydrocarbon.

The invention permits the temperature of the liquid hydrocarbon to be maintained below a set maximum temperature without the use of expensive cooling equipment for the hot rerun catalyst. This is desirable since higher temperatures in the acid settler vessel produce higher pressures in the vessel which can limit throughput capacity (i.e. olefins charge rate). This in turn causes higher pressure on the recycled liquid HF catalyst charged to the alkylation reactor.

In response to a detected increase in the temperature of the hydrocarbon temperature phase in the acid settler vessel above a set point, the flow of hot rerun catalyst vapor to the hydrocarbon phase will be decreased. If an overall constant flow of catalyst vapor to the acid settler vessel is desired, means for flow of rerun catalyst vapor to the catalyst phase can be provided, and the flow of rerun catalyst vapor correspondingly increased in response to a decrease in flow to the hydrocarbon phase. The increased heat from the hot rerun catalyst vapor entering the catalyst phase in the acid settler vessel is then removed from the bottom portion of the vessel.

One embodiment of the invention process and apparatus is shown in the FIGURE and is described below in terms of the HF catalyzed alkylation of an isoparaffin with an olefin.

Referring to the drawing, the isoparaffinic feed is introduced through line 1, the olefinic feed through line 2 and the HF catalyst through line 3. During normal operations, the isoparaffin feed, olefin feed and catalyst feed are introduced as a mixture or individually at the lower end of reaction vessel 4. The reactors, coolers, and other parts of the system contain an inventory of catalyst such that the level of catalyst in the reaction zone extends into acid settler vessel 5. The volume of catalyst present in the alkylation system thus substantially exceeds the volume of hydrocarbon feed and hence constitutes a continuous phase in the system.

Effluent from reaction vessel 4 is discharged through line 6 to an acid settler vessel 5. In acid settler vessel 5 the effluent is separated into a hydrocarbon phase, located in the upper portion of the acid settler vessel 5, and a catalyst phase, located in the lower portion of the acid settler vessel 5. The hydrocarbon phase is discharged through line 7 to fractionator 8, from which isoparaffin is separated from the reaction mixture and is recycled to the system through line 10. Recycled catalyst is removed from the reaction mixture in stripper 9 and recycled to the system through line 11. The remainder of the hydrocarbon product is then further processed in accordance with conventional practices. The catalyst phase is withdrawn from the lower portion of the acid settler vessel 5. A first portion of the catalyst phase passes through line 12 to cooler 13 for recycle to reaction vessel 4 via line 3. A second portion of the catalyst phase passes through line 12 to heater 14. The heated catalyst phase then passes through line 15 to rerun separator column 16. In the rerun separator column 16, the catalyst phase is separated into a bottoms product comprising principally water and some acid-soluble oil, which is discharged via line 17. The overhead fraction from the rerun separator, comprising hot rerun catalyst vapor and any isoparaffin present in the catalyst phase is discharged through line 18.

The invention has the object of maintaining the temperature of the liquid hydrocarbon passed from acid settler vessel 5 to fractionator 8 below a preselected value. Temperature transducer 31 in combination with a temperature sensing device such as a thermocouple, which is operably located in conduit 7, provides an output signal 32 which is representative of the actual temperature of the hydrocarbon phase flowing through conduit 7 which corresponds directly to the temperature of the hydrocarbon phase in the upper portion of the acid settler vessel 5. Signal 32 is provided as the process variable input to the temperature controller 34. The temperature controller 34 is also provided with a set point signal 35 which is representative of a maximum desired temperature for the hydrocarbon phase in the upper portion of the acid settler vessel 5.

The temperature controller 34 may utilize the various modes of control such as proportional, proportional-integral, proportional-derivative, or proportional-integral-derivative. In this preferred embodiment, temperature controller 34 is a proportional-integral-derivative controller but any controller capable of accepting two input signals and producing a scaled output signal, representative of a comparison of the two input signals, is within the scope of the invention.

The scaling of an output signal by a controller is well known in control system art. Essentially, the output of a controller may be scaled to represent any desired factor or variable. In the present case, as will be more fully described hereinafter, the output of temperature controller 34 will be scaled so as to be representative of a desired valve position.

In response to signals 32 and 35, the temperature controller 34 provides an output signal 36 which is responsive to the difference between signals 32 and 35. As previously stated, signal 36 is scaled so as to be representative of the position of the control valve 22 required to maintain the actual temperature of the hydrocarbon phase in the acid settler vessel 5 at or below the temperature represented by signal 35. Signal 36 is provided from the temperature controller 34 as the control signal for control valve 22 and control valve 22 is manipulated in response thereto.

Essentially, control valve 22 will be manipulated in such a manner that control valve 22 will be fully open with respect to flow through line 19 until such time as the temperature represented by signal 32 begins to exceed the temperature represented by signal 35. When this condition begins to occur, control valve 22 will begin to restrict flow through line 19 and divert the thus restricted flow to the catalyst phase located in the lower portion of the acid settler vessel 5 through line 20. In this manner, the temperature of the hydrocarbon phase in the acid settler vessel 5 is maintained at or below the maximum temperature represented by signal 35.

As the temperature of the hydrocarbon stream from the acid settling vessel 5 in line 7 increases, the flow of hot rerun catalyst entering the hydrocarbon phase through line 19 will be decreased, while the flow of hot rerun catalyst entering the catalyst phase in the acid settler vessel 5 through line 20 will be correspondingly increased. The increased hot rerun catalyst entering the catalyst phase in the acid settler vessel 5 is removed from the bottom of the acid settler vessel 5 through line 12.

Thus, depending upon the temperature of the liquid hydrocarbon discharged from line 7 of the acid settler vessel 5, as detected by the temperature controller 34, the hot rerun catalyst in line 18 will be passed to acid settler vessel 5 through line 19 to the hydrocarbon phase located in the upper portion of the acid settler vessel or thorugh line 20 to the catalyst phase located in the lower portion of the acid settler vessel 5.

EXAMPLE

Using the process of the invention shown in FIG. 1, the following operating conditions were calculated for two limiting cases: (1) all of the rerun overhead being condensed in the hydrocarbon phase; and (2) all of the rerun overhead being condensed in the acid phase.

|  | Case I | Case II |
| --- | --- | --- |
| Rerun vapor condensed in | HC phase | Acid phase |
| Acid Phase Temperature, °F. | 100 | 105 |
| Tray temperatures, °F. | 132 | 105 |
| Hydrocarbon Phase Temperature, °F. | 132 | 105 |
| Settler pressure[1] (psig) | 120 | 90 |

[1] at top of vessel

Calculations were based upon a butylene alkylation feed. The cooling water inlet temperature for the acid cooler was 85° F. with a 3.7° F. rise for Case 1 and a 5° F. rise for Case 2. The overall flow of cooling water and area of the exchanger were kept constant.

The above results show that the settler pressure can be controlled at or between the Case I and Case II pressures by varying the flow of rerun vapor and thus the temperature of each settler phase.

Variation and modification are possible within the scope of the invention as described herein. One skilled in the art in possession of this disclosure having studied the same will understand that various engineering details of operation are necessarily omitted for sake of simplicity.

We claim:

1. A method for controlling the temperature or pressure in the hydrocarbon phase of an acid catalyst settler vessel in a catalytic alkylation process, said method comprising:
    (a) introducing alkylation reactor effluent into said settler vessel;
    (b) continuously separating said effluent, in said settler vessel, into a hydrocarbon phase occupying the upper portion of said settler vessel and an acid catalyst phase occupying the lower portion of said settler vessel;
    (c) continuously removing hydrocarbon as product from said upper portion of said settler vessel;
    (d) continuously removing catalyst from said lower portion of said settler vessel;
    (e) processing a portion of the catalyst removed from said settler vessel in a catalyst rerun vessel;
    (f) recycling hot hydrocarbon vapor and hot acid catalyst vapor from said rerun vesel to said settler vessel; and
    (g) apportioning the amount of hot hydrocarbon vapor and hot acid catalyst recycled to the hydrocarbon phase to maintain the temperature or pressure of said hydrocarbon phase within a desired range with hot hydrocarbon vapor and hot acid catalyst vapor in excess of the amount suitable for recycle to said hydrocarbon phase being recycled to said acid catalyst phase.

2. A method of claim 1 wherein said amount of hot hydrocarbon vapor and hot acid catalyst vapor recycle to the hydrocarbon phase of said acid catalyst settler vessel is apportioned by a process comprising:

establishing a first signal representative of the actual value of said (1) temperature, or (2) pressure associated with said hydrocarbon phase in said settler vessel;

establishing a second signal representative of a desired maximum value for said (1) temperature, or (2) pressure;

comparing said first signal and said second signal and establishing a third signal which is responsive to the difference between said first signal and said second signal; and manipulating the flow of said rerun catalyst stream to said hydrocarbon phase in said settler vessel in response to said third signal so as to seek to maintain the actual value of said (1) temperature, or (2) pressure substantially equal to the desired maximum value represented by said second signal.

3. A method in accordance with claim 2, wherein said third signal is scaled so as to be representative of the position of a control valve required to seek to maintain the actual value of said (1) temperature, or (2) pressure substantially equal to the desired maximum value represented by said second signal.

4. A method in accordance with claim 3, wherein said control valve will be fully open with respect to the flow of said rerun catalyst stream to said hydrocarbon phase in said acid settler vessel until such time as said (1) temperature, or (2) pressure represented by said first signal begins to exceed said (1) temperature, or (2) pressure represented by said second signal, wherein said control valve will begin to restrict flow of said rerun catalyst stream to said alkylate product phase in said acid settler vessel and divert the flow of said rerun catalyst stream to said catalyst phase in said settler vessel.

5. An apparatus for controlling the temperature or pressure in the hydrocarbon phase of an acid catalyst separation is a catalytic alkylation process, said apparatus comprising:

(a) an acid catalyst settler vessel having means for introducing alkylation reaction effluent thereinto;
(b) means for removing hydrocarbon as product from the upper portion of said acid catalyst settler vessel;
(c) means for removing acid catalyst from the lower portion of said acid catalyst settler vessel;
(d) means for processing a portion of said acid catalyst removed from said lower portion of said acid catalyst settler vessel to produce a stream of hot recycle material;
(e) means for recycling hot recycle material to each of said upper portion and said lower portion of said acid catalyst settler vessel;
(f) means for apportioning an amount of recycled material to said upper portion of said acid catalyst settler vessel to maintain the temperature or pressure of said upper portion within a desired range; and
(g) means for apportioning to said lower portion of said acid catalyst settler vessel the amount of recycled material in excess of the amount suitable for recycle to said upper portion of said acid catalyst settler vessel.

6. An apparatus of claim 5 wherein said apparatus for apportioning recycled materials comprises:

(a) a (1) temperature, or (2) pressure sensing device;
(b) a (1) temperature, or (2) pressure transducer;
(c) a means for establishing a first signal from said (1) temperature, or (2) pressure sensing device and said (1) temperature, or (2) pressure transducer which is representative of the actual value of a (1) temperature, or (2) pressure associated with said hydrocarbon phase in said acid catalyst settler vessel;
(d) a (1) temperature, or (2) pressure controller containing a set point signal;
(e) a means for establishing a second signal from said set point signal of said (1) temperature, or (2) pressure controller which is representative of a desired maximum value of said (1) temperature, or (2) pressure;
(f) means for comparing said first signal and said second signal and establishing a third signal from said (1) temperature, or (2) pressure controller which is responsive to the difference between said first signal and said second signal;
(g) means for manipulating the flow of said rerun catalyst stream to said hydrocarbon phase in said acid catalyst settler vessel in response to said third signal from said (1) temperature, or (2) pressure controller so as to maintain the actual value of said (1) temperature, or (2) pressure substantially equal to and less than the desired maximum value represented by said second signal.

7. An apparatus in accordance with claim 6, wherein said third signal is representative of the position of a control valve, and wherein a control valve is utilized to maintain the actual value of said (1) temperature, or (2) pressure substantially equal to or less than the desired maximum value represented by said second signal.

8. An apparatus in accordance with claim 6, wherein said means for manipulating the flow of said rerun catalyst is a control valve that will be fully open with respect to the flow of said rerun catalyst stream to the hydrocarbon phase in said acid catalyst settler vessel until such time as the (1) temperature, or (2) pressure represented by said first signal begins to exceed the (1) temperature, or (2) pressure represented by said second signal, wherein the control valve will begin to restrict flow of said rerun catalyst stream to said hydrocarbon phase in said acid catalyst settler vessel and divert the flow of said rerun catalyst stream to said catalyst phase in said acid catalyst settler vessel.

* * * * *